United States Patent [19]

Haga et al.

[11] Patent Number: 5,102,884

[45] Date of Patent: Apr. 7, 1992

[54] SUBSTITUTED BENZOYLUREA COMPOUNDS OR THEIR SALTS, PROCESSES FOR THEIR PRODUCTION AND ANTITUMOUR COMPOSITIONS CONTAINING THEM

[75] Inventors: Takahiro Haga; Nobutoshi Yamada; Hideo Sugi; Toru Koyanagi; Hiroshi Okada, all of Kusatsu, Japan

[73] Assignee: Ishihara Sangyo Kaisha Ltd., Osaka, Japan

[21] Appl. No.: 554,449

[22] Filed: Jul. 19, 1990

[30] Foreign Application Priority Data

Jul. 28, 1989 [JP] Japan ................................. 1-195883
Dec. 12, 1989 [JP] Japan ................................. 1-322094
Apr. 27, 1990 [JP] Japan ................................. 2-113529

[51] Int. Cl.$^5$ ............... A61K 31/535; A61K 31/505; C07D 413/00; C07D 239/02
[52] U.S. Cl. ............... 514/235.8; 514/274; 544/123; 544/316
[58] Field of Search ............... 544/316, 123; 514/274, 514/235.8

[56] References Cited

U.S. PATENT DOCUMENTS

| | | | |
|---|---|---|---|
| 4,677,110 | 6/1987 | Haga et al. | 514/274 |
| 4,677,111 | 6/1987 | Haga et al. | 514/274 |
| 4,727,077 | 2/1988 | Haga et al. | 514/274 |
| 4,987,135 | 1/1991 | Haga et al. | 514/274 |

FOREIGN PATENT DOCUMENTS

| | | |
|---|---|---|
| 164694 | 12/1985 | European Pat. Off. |
| 178572 | 4/1986 | European Pat. Off. |
| 192235 | 8/1986 | European Pat. Off. |
| 193249 | 9/1986 | European Pat. Off. |
| 226104 | 6/1987 | European Pat. Off. |
| 335408 | 10/1989 | European Pat. Off. |

*Primary Examiner*—Mukund J. Shah
*Assistant Examiner*—Matthew V. Grumbling
*Attorney, Agent, or Firm*—Oblon, Spivak, McClelland, Maier & Neustadt

[57] ABSTRACT

A substituted benzoylurea compound of the formula (I):

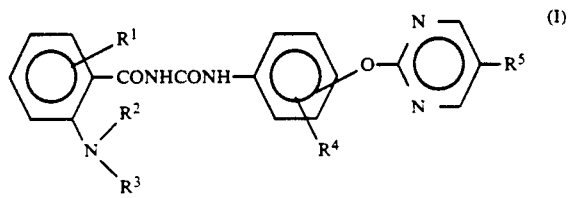

wherein $R^1$ is a hydrogen atom, a halogen atom or a nitro group, each of $R^2$ and $R^3$ is a hydrogen atom, an alkyl group, —$COR^6$ (wherein $R^6$ is an alkyl group or an alkoxy group) or —$SO_2R^6$ (wherein $R^6$ is as defined above), or $R^2$ and $R^3$ may form together with the adjacent nitrogen atom a heterocyclic ring, $R^4$ is a halogen atom, a substituted or unsubstituted alkyl group, a substituted or unsubstituted alkoxy group, a substituted or unsubstituted alkylthio group or a nitro group, and $R^5$ is a halogen atom, a nitro group or a substituted or unsubstituted alkyl group, or its salt.

12 Claims, No Drawings

SUBSTITUTED BENZOYLUREA COMPOUNDS OR THEIR SALTS, PROCESSES FOR THEIR PRODUCTION AND ANTITUMOUR COMPOSITIONS CONTAINING THEM

The present invention relates to novel substituted benzoylurea compounds or their salts, having an N-substituted benzoyl group on one side of the urea chain and a substituted pyrimidinyloxyphenyl group on the other side, processes for their production, intermediates thereof, compositions for treating a cancer such as leukemia, melanoma, sarcoma or carcinoma which comprise the substituted benzoylurea compounds or their salts, and a method for treating such a cancer.

Those similar to the substituted benzoylurea compounds of the present invention are disclosed in European Patent Publication No. 193249. However, the compounds of the present invention are different from them in the chemical structure with respect to the substituent bonded to the phenyl ring directly bonded to the urea group. Further, the compounds of the present invention are superior on the antitumour activities to the compounds disclosed in the above publication. Further, European Patent Publication No. 335408 discloses benzoylurea compounds. However, these compounds and the compounds of the present invention are different in the chemical structure with respect to the presence or absence of the substituent at the carbon atom or the nitrogen atom of the carbonylurea chain and with respect to the type of the substituent to the amino group as the substituent on the benzoyl group.

Further, the compounds of the present invention are superior to the conventional benzoylurea compounds in the solubility to a non-aqueous solvent.

The present inventors have found that the substituted benzoylurea compounds of the following formula (I) and their salts show a high level of antitumour activities, and they have an improved solubility in a non-aqueous solvent while the conventional benzoylurea compounds tend to be hardly soluble in a non-aqueous solvent. The present invention has been accomplished on the basis of these discoveries.

The present invention provides a substituted benzoylurea compound of the formula (I):

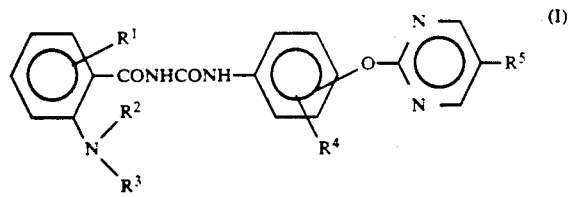

wherein $R^1$ is a hydrogen atom, a halogen atom or a nitro group, each of $R^2$ and $R^3$ is a hydrogen atom, an alkyl group, —$COR^6$ (wherein $R^6$ is an alkyl group or an alkoxy group) or —$SO_2R^6$ (wherein $R^6$ is as defined above), or $R^2$ and $R^3$ may form together with the adjacent nitrogen atom a heterocyclic ring, $R_4$ is a halogen atom, a substituted or unsubstituted alkyl group, a substituted or unsubstituted alkoxy group, a substituted or unsubstituted alkylthio group or a nitro group, and $R^5$ is a halogen atom, a nitro group or a substituted or unsubstituted alkyl group, or its salt.

The present invention also provides processes for the production of the compound of the formula (I) or its salt, an intermediate thereof, a composition for treating a cancer such as leukemia, melanoma, sarcoma or carcinoma, which comprises the compound of the formula (I) or its salt, and a method for treating such a cancer.

Now, the present invention will be described in detail with reference to the preferred embodiments.

In the formula (I), the substituent of the substituted alkyl group, the substituted alkoxy group and the substituted alkylthio group in the definition of $R^4$ includes, for example, a halogen atom, an alkoxy group, an alkylthio group, a cyano group, a thiocyanate group, an alkoxycarbonyl group, a carboxyl group and an alkylthiocarbonyl group. The substituent of the substituted alkyl group in the definition of $R^5$ may be a halogen atom. The number of substituents contained in $R^4$ and $R^5$ may be one or more.

The heterocyclic group formed by $R^2$ and $R^3$ together with the adjacent nitrogen atom, may be a morpholino group, an aziridinyl group, a pyrrolidinyl group, a piperidino group or a pyrrolyl group.

The salt of the benzoylurea compound of the present invention may be any salt so long as it is pharmaceutically acceptable. For example, it may be a salt of a hydrogen halide such as hydrochloric acid or hydrobromic acid, or a salt of an alkali metal such as sodium or potassium, or of an alkaline earth metal such as magnesium or calcium.

The halogen atom in the definition of $R^1$, $R^4$ and $R^5$, includes a fluorine atom, a chlorine atom, a bromine atom and an iodine atom.

In the formula (I), the alkyl moiety constituting the alkyl group and the alkoxy group in the definition of $R^2$ and $R^3$, the alkyl moiety constituting the substituted or unsubstituted alkyl group, the substituted or unsubstituted alkoxy group and the substituted or unsubstituted alkylthio group in the definition of $R^4$, the alkyl moiety constituting the substituted or unsubstituted alkyl group in the detimition of $R^5$, and the alkyl moiety constituting the alkoxy group, the alkylthio group, the alkoxycarbonyl group or the alkylthio carbonyl group as the substituent of the substituted alkyl group, the substituted alkoxy group and the substituted alkylthio group in the definition of $R^4$, is preferably an alkyl group having from 1 to 10 carbon atoms such as a methyl group, an ethyl group, a propyl group, a butyl group, a pentyl group, a hexyl group, a heptyl group, an octyl group, a nonyl group or a decyl group, more preferably an alkyl group having from 1 to 4 carbon atoms. Further, these alkyl group also include linear or branched aliphatic chain structural isomers.

In the above formula (I), a substituted benzoylurea compound of the following formula (I') or its salt, is preferred:

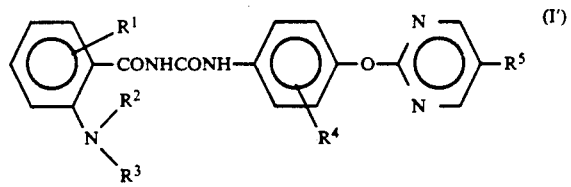

wherein $R^1$, $R^2$, $R^3$, $R^4$ and $R^5$ are as defined above.

$R^1$ is preferably a hydrogen atom. Each of $R^2$ and $R^3$ is preferably an alkyl group. Also preferably, $R^2$ and $R^3$ form together with the adjacent nitrogen atom a heterocyclic ring. $R^4$ is preferably a halogen atom or a substituted or unsubstituted alkyl group, more preferably a substituted or unsubstituted alkyl group. $R^5$ is preferably a halogen atom. The following compounds are preferred among the substituted benzoylurea compounds of the formula (I) and their salts:

N-[4-(5-bromo-2-pyrimidinyloxy)-3-methylphenyl]-N'-(dimethylamino)benzoyl]urea, N-[4-(5-bromo-2-pyrimidinyloxy)-3-methylphenyl]-N'-[2-(dimethylamino)benzoyl]urea.hydrochloride, N-[4-(5-bromopyrimidinyloxy)-3-trifluoromethylphenyl]-N'-[2(dimethylamino)benzoyl]urea, N-[4-(5-chloro-2-pyrimidinyloxy)-3-trifluoromethylphenyl]-N'-[2-(dimethylamino)benzoyl]urea, N-[4-(5-chloro-2-(pyrimidinyloxy)-3-methylphenyl]-N'-[2-(dimethylamino)benzoyl]urea, N-[4-(5-bromo-2-pyrimidinyloxy)-3-methylphenyl]-N'-[2(diethylamino)-benzoyl]urea, and N-[4-(5-chloro-2-pyrimidinyloxy)-3-methylphenyl]-N'-[2-(diethylamino)benzoyl]urea.

The benzoyl urea compound of the formula (I) can be prepared by the following methods:

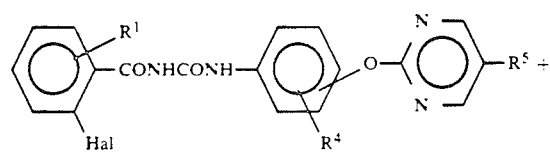

(II)

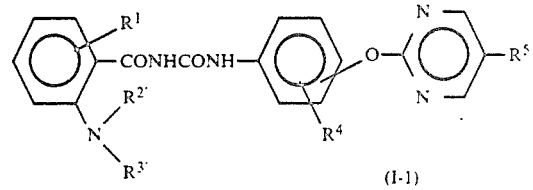

(III)

wherein $R^1$, $R^2$, $R^3$, $R^4$ and $R^5$ are as defined above, and Hal is a halogen atom.

This reaction is conducted usually at a temperature of from 0° C. to a reflux temperature, and the reaction time is usually from 1 to 24 hours. A solvent may be used for this reaction. Such a solvent includes, for example, benzene, toluene, xylene, chlorobenzene, hexane, chloroform, methylene chloride, dichloroethane, diethyl ether, tetrahydrofuran, dioxane, ethyl acetate, dimethylformamide, dimethylsulfoxide, hexamethylphosphoric triamide, and water.

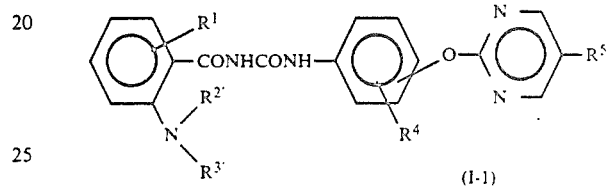

wherein $R^1$, $R^4$ and $R^5$ are as defined above, each of $A^1$ and $A^2$ is —NCO or —NH$_2$, provided that when $A^1$ is —NCO, $A^2$ is —NH$_2$, and when $A^1$ is —NH$_2$, $A^2$ is —NCO, and each of $R^{2'}$ and $R^{3'}$ is an alkyl group, —COR$^6$ (wherein $R^6$ is an alkyl group or an alkoxy group) or —SO$_2$R$^6$ (wherein $R^6$ is as defined above), or $R^{2'}$ and $R^{3'}$ may form together with the adjacent nitrogen atom a heterocyclic ring.

This reaction is conducted usually in the presence of a solvent at a temperature of from 0° C. to a reflux temperature, and the reaction time is usually from 1 to 24 hours. The solvent includes, for example, benzene, toluene, xylene, chlorobenzene, hexane, chloroform, methylene chloride, dichloroethane, diethyl ether, tetrahydrofuran, dioxane, ethyl acetate, dimethylformamide, dimethylsulfoxide and hexamethylphosphoric triamide.

wherein $R^1$, $R^4$ and $R^5$ are as defined above, and $B^1$ is a phthaloyl group.

The hydrazine may be hydrazine, an alkyl hydrazine or phenyl hydrazine.

This reaction is conducted usually in the presence of a solvent at a temperature of from 0° C. to a reflux temperature, and the reaction time is usually from 1 to 24 hours. The solvent includes, for example, methanol, ethanol, chloroform, and methylene chloride.

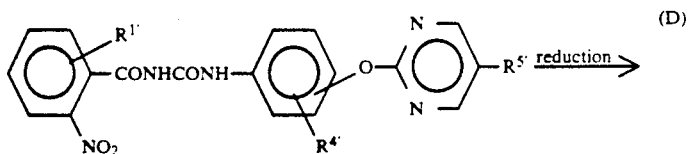

wherein $R^{1'}$ is a hydrogen atom or a halogen atom, $R^{4'}$ is a halogen atom, a substituted or unsubstituted alkyl group, a substituted or unsubstituted alkoxy group or a substituted or unsubstituted alkylthio group, and $R^{5'}$ is a halogen atom or a substituted or unsubstituted alkyl group.

This reaction is conducted in accordance with a usual reduction method. The reduction method may, for example, be a reduction method using a metal such as reduced iron or zinc, or a catalytic reduction method using a catalyst such as platinum or palladium-carbon. The reaction is conducted usually at a temperature of from 0° C. to a reflux temperature, and the reaction time is usually from 1 to 100 hours.

wherein $R^1$, $R^4$ and $R^5$ are as defined above, and $R^{2''}$ is an alkyl group.

This reaction is conducted usually at a temperature of from 0° C. to a reflux temperature, and the reaction time is usually from 0.1 to 24 hours. A solvent and a base may be used for this reaction. The solvent includes, for example, benzene, toluene, xylene, chlorobenzene, pyridine, hexane, cyclohexane, chloroform, methylene chloride, dichloroethane, diethyl ether, tetrahydrofuran, dioxane, ethyl acetate, dimethylformamide, dimethylsulfoxide and hexamethylphosphoric triamide. The base includes an organic lithium such as n-butyl lithium, tert-butyl lithium or phenyl lithium, an inorganic base such as sodium hydroxide, potassium hydroxide, sodium hydride or potassium hydride, and an organic base such as triethylamine or pyridine.

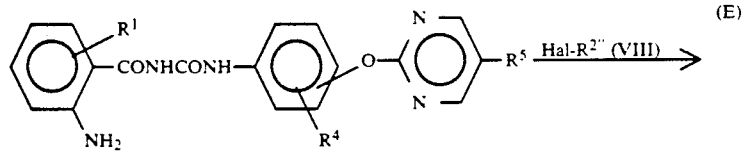

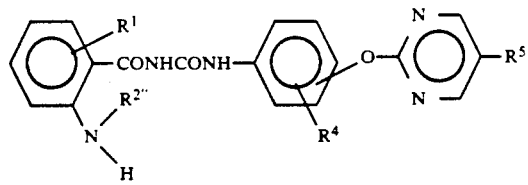

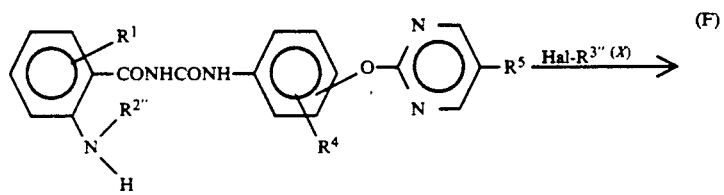

-continued

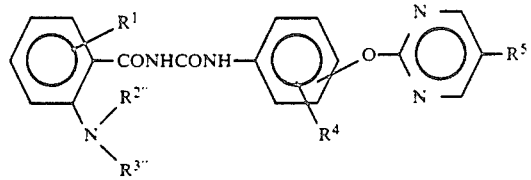

(XI)

wherein $R^1$, $R^{2'''}$, $R^4$ and $R^5$ are as defined above, and $R^{3''}$ is an alkyl group.

The reaction conditions may be the same as described above with respect to (E).

Further, the compounds of the formula (II) and (VII) can be prepared in accordance with the above method (B). A compound of the formula (IV) wherein $A^1$ is $-NH_2$, can be prepared, for example, by reacting a 2-halogenobenzamide with a secondary amine of the formula (III) in accordance with the above method (A), and a compound wherein $A^1$ is NCO can be prepared by reacting the benzamide obtained by the above method, with oxalyl chloride at a temperature of from 0° C. to a reflux temperature for from 1 to 100 hours in the presence of the same solvent as mentioned in the above method (B). Further, a compound of the formula (VI) can be prepared in accordance with the above method (B) by using either a benzamide obtained by reacting a 2-aminobenzamide with phthalic anhydride at a temperature of from 0° C. to a reflux temperature for from 1 to 100 hours in the presence of a solvent such as chloroform, methylene chloride or pyridine, or an isocyanate obtained by reacting the benzamide obtained by the above-mentioned method, with oxalyl chloride at a temperature of from 0° C. to a refluxing temperature for 1 to 100 hours in the presence of the same solvent as mentioned in the above method (B).

Further, the salt of the substituted benzoylurea compound can readily be obtained by a usual production method.

Among the compounds of the formula (IV), those wherein $R^{2'}$ and $R^{3'}$ are $-COR^6$ (wherein $R^6$ is an alkyl group or an alkoxy group or $-SO_2R^6$ (wherein $R^6$ is as defined above) (as represented by the following formula (XII)) are novel. Among the compounds of the formula (XII), those wherein $A^1$ is $-NH_2$ are preferred.

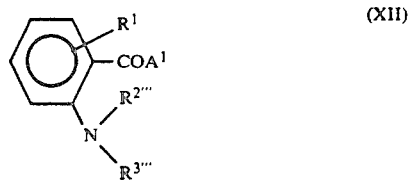

(XII)

wherein each of $R^{2'''}$ and $R^{3'''}$ is an alkyl group, COR6 (wherein $R^6$ is an alkyl group or an alkoxy group) or $-SO_2R^6$ (wherein $R^6$ is as defined above), provided that either one of $R^{2'''}$ and $R^{3'''}$ is $-COR^6$, $-SO_2R^6$, and $R^1$ and $A^1$ are as defined above.

Now, specific Preparation Examples of the compounds of the formula (I) will be described.

PREPARATION EXAMPLE 1

Preparation of N-[4-(5-bromo-2-pyrimidinyloxy)-3methylphenyl]-N'-[2-(dimethylamino)benzoyl]urea (Compound No. 1 as described hereinafter)

A solution of a mixture comprising 3.73 g of 4-(5-bromo-2-pyrimidinyloxy)-3-methylphenyl isocyanate, 2.0 g of 2-(dimethylamino)benzamide and 45 ml of toluene, was reacted under reflux for 4 hours.

After completion of the reaction, the mixture was cooled, and insoluble substances were removed by filtration. The filtrate thereby obtained was concentrated and purified by silica gel column chromatography (developing solvent; n-hexane:ethyl acetate=6:4) to obtain 3.9 g of the desired product (melting point: 98°-104° C.) (Compound No. 1 as described hereinafter).

PREPARATION EXAMPLE 2

Preparation of N-[4-(5-bromo-2-pyrimidinyloxy)-3methylphenyl]-N'-[2-(dimethylamino)benzoyl]urea hydrochloride (Compound No. 2 as described hereinafter)

1.5 g of the desired product obtained in Example 1 (Compound No. 1 as described hereinafter) was dissolved in 20 ml of diethyl ether and 50 ml of methylene chloride, and hydrochloric acid gas was introduced to the solution and saturated therein.

Thereafter, the saturated solution was stirred for one hour and then cooled, and precipitated crystals were collected by filtration. The crystals thus obtained were washed with diethyl ether to obtain 1.55 g of the desired product (melting point: 117°-123° C.) (Compound No. 2 as described hereinafter).

PREPARATION EXAMPLE 3

Preparation of N-(2-aminobenzoyl)-N'-[4-(5-bromo-2-pyrimidinyloxy)-3-chlorophenyl]urea (Compound No. 26 as described hereinafter)

A mixture comprising 1.0 g of N-[4-(5-bromo-2-pyrimidinyloxy)-3-chlorophenyl]-N'-(2-nitrobenzoyl) urea and 30 ml of glacial acetic acid, was heated to 80° C., and 0.57 g of reduced iron was gradually added thereto under stirring. Thereafter, the mixture was stirred and reacted at the same temperature for 30 minutes.

After completion of the reaction, the reaction mixture was poured into water, and the insoluble product was collected by filtration. The collected insoluble product was dried under vacuum and purified by silica gel column chromatography (developing solvent; n-hexane:ethyl acetate=7:3) to obtain 0.4 g of the desired product (melting point: 196°-200° C.) (Compound No. 26 as described hereinafter).

PREPARATION EXAMPLE 4

Preparation of
N-[4-(5-bromo-2-pyrimidinyloxy)-3-methylphenyl]-N'-(2-morpholinobenzoyl)urea (Compound No. 34 as described hereinafter)

(1) 5 g of 2-fluorobenzamide and 25 ml of morpholine were reacted in an autoclave at 100° C. for 18 hours.

After completion of the reaction, the reaction product was cooled, and excess morpholine was distilled off. The residue was purified by silica gel column chromatography (developing solvent; n-hexane:ethyl acetate=3:7) to obtain 2.8 g of 2-morpholinobenzamide (melting point: 112°-119° C).

(2) A solution obtained by dissolving 3.28 g of 4-(5-bromo-2-pyrimidinyloxy)-3-methylphenyl isocyanate in 30 ml of toluene, was dropwise added to 2.21 g of 2-morpholinobenzamide obtained in the above step (1) under stirring. Thereafter, the mixture was reacted at 100° C. for 3 hours.

After completion of the reaction, toluene was distilled off, and the residue was purified by silica gel column chromatography (developing solvent; n-hexane:ethyl acetate=1:1) to obtain 1.25 g of the desired product (melting point: 67°-70° C., amorphous) (Compound No. 34 as described hereinafter).

PREPARATION EXAMPLE 5

Preparation of
N-[4-(5-chloro-2-pyrimidinyloxy)-3methylphenyl]-N'-[2-(dimethylamino)benzoyl]urea (Compound No. 11 as described hereinafter)

A solution of a mixture comprising 3.33 g of 4-(5-chloro-2-pyrimidinyloxy)-3-methylphenyl isocyanate, 2.1 g of 2-(dimethylamino)benzamide and 30 ml of toluene, was reacted at 100° C. for 4 hours.

After completion of the reaction, the solution mixture was cooled, and insoluble substances were removed by filtration. The filtrate thereby obtained was concentrated and purified by silica gel column chromatography (developing solvent; n-hexane:ethyl acetate=6:4) to obtain 2.84 g of the desired product (melting point: 48°-52° C., amorphous) (Compound No. 11 as described hereinafter).

PREPARATION EXAMPLE 6

Preparation of N-[4-(5-bromo-2-pyrimidinyloxy)-3-methylphenyl]-N'-[2-)diethylamino)benzoyl]urea (Compound No. 33 as described hereinafter)

A solution of a mixture comprising 3.27 g of 4-(5-bromo-2-pyrimidinyloxy)-3-methylphenyl isocyanate, 2.05 g of 2-(diethylamino)benzamide and 30 ml of toluene, was reacted at 100° C. for 3 hours.

After completion of the reaction, the solution mixture was cooled, and insoluble substances were removed by filtration. The filtrate thereby obtained was concentrated and purified by silica gel column chromatography (developing solvent; n-hexane:ethyl acetate=7:3) to obtain 1.45 g of the desired product (melting point: 39°-43° C., amorphous) (Compound No. 33 as described hereinafter).

PREPARATION EXAMPLE 7

Preparation of
N-[2-(acetylamino]benzoyl]-N'-[4-(5-bromo-2-pyrimidinyloxy)-3-methylphenyl]urea (Compound No. 49 as described hereinafter)

1.3 g of N-(2-aminobenzoyl)-N'-[4-(5-bromo-2-pyrimidinyloxy)-3-methylphenyl]urea (Compound No. 27 as described hereinafter) as prepared in accordance with Preparation Example 3, was added to 30 ml of pyridine, and 0.25 ml of acetyl chloride was dropwise added thereto under cooling with ice. The mixture was stirred at room temperature for 2 hours and 30 minutes. Then, pyridine was distilled off, and the residue was purified by silica gel column chromatography (developing solvent; methylene chloride:ethyl acetate=7:3) to obtain 1.18 g of the desired product (melting point: 186°-191° C.) (Compound No. 49 as described hereinafter).

Now, typical examples of the compound of the formula (I) will be given in Table 1.

TABLE 1

| Compound No. | R¹ | R² | R³ | R⁴ | R⁵ | salt | Type of Physical properties |
|---|---|---|---|---|---|---|---|
| 1 | H | CH₃ | CH₃ | 3-CH₃ | Br | — | M.P. 98–104° C. |
| 2 | H | CH₃ | CH₃ | 3-CH₃ | Br | HCl | M.P. 117–123° C. |
| 3 | 6-F | CH₃ | CH₃ | 3-CH₃ | Br | — | M.P. 79–88° C. (amorphous) |
| 4 | 6-F | CH₃ | CH₃ | 3-Cl | Br | — | M.P. 81–97° C. (amorphous) |
| 5 | 4-Cl | CH₃ | CH₃ | 3-OCH₃ | Br | — |  |
| 6 | 5-Cl | CH₃ | CH₃ | 3-F | Br | — |  |
| 7 | H | 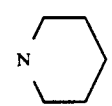 |  |  | 3-C₂H₅ | Br | — |

TABLE 1-continued

[Structure: Ar(R¹)(NR²R³)–CONHCONH–Ar(R⁴)–O–pyrimidine(R⁵); with NR²R³ group shown]

| Compound No. | R¹ | R² | R³ | R⁴ | R⁵ | salt | Type of Physical properties |
|---|---|---|---|---|---|---|---|
| 8 | H | C₂H₅ | C₂H₅ | 3-CH₂CN | Br | — | |
| 9 | H | CH₃ | CH₃ | 3-CF₃ | Br | — | M.P. 127–129° C. |
| 10 | H | CH₃ | CH₃ | 3-CF₃ | Cl | — | M.P. 122–125° C. |
| 11 | H | CH₃ | CH₃ | 3-CH₃ | Cl | — | M.P. 48–52° C. (amorphous) |
| 12 | H | CH₃ | CH₃ | 3-Cl | Cl | — | |
| 13 | H | CH₃ | CH₃ | 3-NO₂ | Br | — | M.P. 68–71° C. (amorphous) |
| 14 | H | CH₃ | CH₃ | 3-CH₂OCH₃ | Br | — | |
| 15 | H | CH₃ | CH₃ | 3-CH₂SCH₃ | Br | — | |
| 16 | H | CH₃ | CH₃ | 3-CH₂SCN | Br | — | |
| 17 | H | CH₃ | CH₃ | 3-CH₂CO₂CH₃ | Br | — | |
| 18 | H | CH₃ | CH₃ | 3-CH₃ | CH₃ | — | |
| 19 | H | CH₃ | CH₃ | 3-CH₃ | CF₃ | — | |
| 20 | H | \<pyridine\> | | 3-CH₃ | Cl | — | |
| 21 | 4-NO₂ | CH₃ | CH₃ | 3-CH₃ | I | — | |
| 22 | 3-F | \<morpholine\> | | 3-CH₃ | F | — | |
| 23 | 4-Br | CH₃ | CH₃ | 3-CH₃ | Cl | — | |
| 24 | H | n-C₄H₉ | n-C₄H₉ | 3-CH₃ | Cl | — | |
| 25 | H | CH₃ | CH₃ | 3-CH₃ | NO₂ | — | |
| 26 | H | H | H | 3-Cl | Br | — | M.P. 196–200° C. |
| 27 | H | H | H | 3-CH₃ | Br | — | M.P. 189–193° C. |
| 28 | H | H | H | 3-CH₃ | Cl | — | |
| 29 | H | H | CH₃ | 3-Cl | Br | — | |
| 30 | H | H | CH₃ | 3-CH₃ | Br | — | |
| 31 | H | H | CH₃ | 3-CH₃ | Cl | — | |
| 32 | H | CH₃ | CH₃ | 2-F | Br | — | |
| 33 | H | C₂H₅ | C₂H₅ | 3-CH₃ | Br | — | M.P. 39–43° C. (amorphous) |
| 34 | H | \<morpholine\> | | 3-CH₃ | Br | — | M.P. 67–70° C. (amorphous) |
| 35 | H | CH₃ | CH₃ | 3-OCH₃ | Cl | — | M.P. 49–53° C. (amorphous) |
| 36 | H | CH₃ | CH₃ | 3-NO₂ | Cl | — | M.P. 136–139° C. (amorphous) |
| 37 | H | \<piperidine\> | | 3-CH₃ | Br | — | M.P. 163–170° C. (amorphous) |
| 38 | H | C₂H₅ | C₂H₅ | 3-CH₃ | Cl | — | |
| 39 | H | CH₃ | CH₃ | 3-C₂H₅ | Br | — | |
| 40 | H | CH₃ | CH₃ | 3-C₃H₇(n) | Br | — | |
| 41 | H | CH₃ | CH₃ | 3-OCH₃ | Br | — | |
| 42 | H | CH₃ | CH₃ | 3-SCH₃ | Br | — | |
| 43 | H | CH₃ | CH₃ | 3-CHF₂ | Br | — | |

TABLE 1-continued structure: Ar-CONHCONH-Ar'-O-pyrimidine-R^5 with R^1, R^2 on first ring (R^2 connected to N-R^3), R^4 on second ring

| Compound No. | R^1 | R^2 | R^3 | R^4 | R^5 | Type of salt | Physical properties |
|---|---|---|---|---|---|---|---|
| 44 | H | $CH_3$ | $CH_3$ | $3-CH_3$ | F | — | |
| 45 | H | $CH_3$ | $CH_3$ | $3-CH_3$ | I | — | |
| 46 | H | $CH_3$ | $C_2H_5$ | $3-CH_3$ | Br | — | R.I. $n_D^{47.2}$ 1.6062 |
| 47 | H | $n-C_3H_7$ | $n-C_3H_7$ | $3-CH_3$ | Br | — | R.I. $n_D^{47.4}$ 1.5400 |
| 48 | H | $n-C_6H_{13}$ | $n-C_6H_{13}$ | $3-CH_3$ | Br | — | R.I. $n_D^{27.7}$ 1.5754 |
| 49 | H | H | $COCH_3$ | $3-CH_3$ | Br | — | M.P. 186-191° C. |
| 50 | H | H | $COC_3H_7(n)$ | $3-CH_3$ | Br | — | M.P. 190-192° C. |
| 51 | H | H | $COC_8H_{17}(n)$ | $3-CH_3$ | Br | — | M.P. 162-164° C. |
| 52 | H | $CH_3$ | $COCH_3$ | $3-CH_3$ | Br | — | M.P. 113-116° C. |
| 53 | H | H | $SO_2CH_3$ | $3-CH_3$ | Br | — | M.P. 149-155° C. |
| 54 | H | $SO_2CH_3$ | $SO_2CH_3$ | $3-CH_3$ | Br | — | M.P. 221-226° C. |
| 55 | H | H | $COCH_3$ | $3-CH_3$ | Br | — | M.P. 233-235° C. |

Remarks
M.P. Melting point
R.I Refractive index

Compound No. 56:
N-[3-(5-chloro-2-pyrimidinyloxy)-4-methylphenyl]-N'-[-2-(dimethylamino)benzoyl]urea (melting point: 134°-136.5° C.)

Compound No. 57:
N-[3-(5-bromo-2-pyrimidinyloxy)-4-methylphenyl]-N'-[2-(dimethylamino)benzoyl]urea Compound No. 58:
N-[3-(5-chloro-2-pyrimidinyloxy)-4-methylphenyl]-N'-[2-(diethylamino)benzoyl]urea Compound No. 59:
N-[3-(5-bromo-2-pyrimidinyloxy)-4-methylphenyl]-N'-[2-(diethylamino)benzoyl]urea Compound No. 60:
N-[3-(5-bromo-2-pyrimidinyloxy)-4trifluoromethylphenyl]-N'-[2(dimethylamino)benzoyl]urea Compound No. 61:
N-[3-(5-bromo-2-pyrimidinyloxy)-4trifluoromethylphenyl]-N'[2(diethylamino)benzoyl]urea The compound of the formula (I) is effective against experimental murine tumors such as P-388 leukemia, L-1210 leukemia, B-16 melanoma, M-5076 sarcoma, Colon 38, Colon 26 and Lewis lung carcinoma. On the other hand, certain in vivo test systems and protocols have been developed by National Cancer Institute for testing compounds to determine their suitabilities as antineoplastic agents. These have been reported in "Cancer Chemotherapy Reports", Part III, Vol. 3, No. 2 (1972) written by Deran, Greenberg, MacDonald, Schumacher and Abott. These protocols have established standardized screening tests which are generally followed in the field of testing for antitumour agents. Among these systems, P-388 leukemia is particularly significant for the present invention. These neoplasms were discovered in mice. Excellent antitumour activities indicated by the percent increase of the medium servival time of treated animals (T) over control animals (C) in these protocols, generally suggest the same results against human leukemia.

Now, the antitumour activity, solubility in a non-aqueous solvent, doses and methods of administration of the compounds of the formula (I) will be described. These compounds exhibit excellent antitumour activities. (1-1) Antitumour activity

TEST EXAMPLE 1

(Intraperitoneally transplanted—intraperitoneally administered)

$1 \times 10^6$ of P-388 leukemia cells per mouse were intraperitoneally transplanted into $BDF_1$ mouse. Each formulation was intraperitoneally administered on days 1 and 8 after the transplantation.

The mortality was observed for 30 days. The increase life span of each group was determined on such basis that the medium survival time of a control group to which physiological saline was administered was regarded to be 0% of increase life span (ILS). The results are shown in Table 2. Among the tested formulations, compound 2 was formulated in accordance with the below-mentioned Formulation Example 9, and the rest was formulated in accordance with the below-mentioned Formulation Example 8.

TABLE 2

| Compound No. | Dose (Active ingredient mg/kg/day) | Increase life span* (ILS) (%) |
|---|---|---|
| 1 | 25 | 183 |
|   | 12.5 | 126 |
| 2 | 25 | 206 |
|   | 12.5 | 94 |
| 3 | 25 | 150 |
|   | 12.5 | 50 |
| 4 | 50 | 135 |
| 9 | 12.5 | 80 |
| 10 | 12.5 | 39 |
| 11 | 50 | 132 |
|   | 25 | 99 |
| 13 | 50 | 27 |
| 26 | 25 | >137 |
|   | 12.5 | 93 |
| 33 | 25 | 49 |
| 34 | 6.25 | 49 |
| 35 | 200 | 53 |

TABLE 2-continued

| Compound No. | Dose (Active ingredient mg/kg/day) | Increase life span* (ILS) (%) |
|---|---|---|
|  | 100 | 27 |
| 36 | 100 | 68 |
| 27 | 25 | 160 |
|  | 12.5 | 126 |
| 49 | 25 | 59 |
|  | 12.5 | 39 |
| 50 | 50 | 150 |
|  | 25 | 49 |
| 51 | 50 | 184 |
| 52 | 12.5 | 139 |
|  | 6.25 | 39 |
| 54 | 50 | 49 |

(Note) *Increase life span is calculated by the following equation:
Increase life span % (ILS) =

$$\left( \frac{\text{Median survival time of test group}}{\text{Median survival time of control animals}} \times 100 \right) - 100$$

(1-2) Antitumour activity

TEST EXAMPLE 2

(intraperitoneally transplanted—intravenously injected)

$1 \times 10^6$ of P-388 leukemia cells per mouse were intraperitoneally transplanted to $BDF_1$ mouse. Each formulation (formulated in accordance with the below-mentioned Formulation Example 10) was intravenously injected from the tail on days 1 and 8 after the transplantation.

The mortality was observed for 30 days. The increase life span (ILS, %) of each treated group was determined on such basis that the median survival time of a control group to which a physiolosical saline was administered was regarded to be 0% of increase life span (ILS). In the cases where Compounds No. 1 and No. 11 were administered at a dose (active ingredient mg/kg/day) of 10 mg/kg, ILS (%) was 46 and 27, respectively. (Note) * The increase life span was calculated in the
same manner as in Test Example 1.
(2) Solubility to a non-aqueous solvent

TEST EXAMPLE 3

A stirring magnet was put into a 10 ml or 100 ml egg plant flask equipped with a stopper, and 50 mg of a test compound was introduced into this flask. Further, a suitable amount of a desired solvent was introduced thereinto, and the solubility was determined. The results are shown in Table 3 (the temperature at the time of measuring the solubility was from 18° to 20° C.).

TABLE 3

| Compound No. | Solubility (%) | |
|---|---|---|
|  | Medium chain triglyceride | Soybean oil |
| 1 | 2.1–2.3 | 0.46–0.49 |
| 11 | 1.5–1.8 | 0.15–0.16 |
| 33 | — | at least 13.6 |

(Note)
As the medium chain triglyceride, ODO, tradename, manufactured by Nisshin Seiyu K.K., was employed.

(3) Dose and method for administration

As the method for administration, in the case of animals, drugs may be administered by injection such as intraperitoneal injection, intravenous injection or local administration, or by oral administration. In the case of human being, drugs may be administered by injection such as intravascular injection to a vein or an arteria or local administration, by oral administration, or as a suppository. The dose is determined in view of the results of animal experiments and various conditions within a range that the total amount does not exceed a certain amount. Drugs may be administered continuously or intermittently. However, the dose may optionally vary depending upon the method for administration, the patient or the condition of an animal to be treated such as age, body weight, sex, sensitivity, food, time of administration, drugs used together or degree of the patient or the disease. The suitable amount and the numbers of administration under a certain condition, must be determined by the determination test of a suitable amount by a specialist based on the above guidelines.

The antitumour agent of the present invention may be formulated in the same manner as in the case of usual drugs. It is formulated from the active ingredient and various pharmaceutically acceptable adjuvants such as an inert diluent. The formulation can be administered orally or intravenously, or in the form of a suppository.

Further, the content of the active ingredient in the antitumour agent of the present invention varies depending upon the difference of various conditions and can not generally be defined. The agent may contain the active ingredient in the same manner as in the case of usual antitumour agents. For example, it may contain at least 0.1% of the active ingredient.

The compound of the formula (I) may be formulated, for example, into a suppository or a capsule by directly mixing the compound with polyethylene glycol, or into an aqueous suspension. When the compound of the formula (I) is formulated into an aqueous suspension, as the method for formulating an aqueous suspension which does not contain a phospholipid, there may be mentioned, for example, a method wherein the active ingredient compound previously formed into fine powder, is added to an aqueous solution containing a surfactant and, if necessary, a defoaming agent, the mixture is then subjected to wet pulverization to obtain particles having a particle size of at most 5 µm, for example, particles of which 80% have a particle size of if necessary, a thickener is added thereto. The surfactant includes, for example, polyoxyethylene hardened castor oil, polyoxyethylene sorbitol fatty acid ester, sucrose ester, polyoxyethylene-polyoxypropylene block polymer and oxyethylated polyarylphenol phosphate. The defoaming agent includes, for example, dimethylpolysiloxane, methylphenylsiloxane, sorbitol fatty acid ester, polyoxyethylene polyoxypropylenecetyl ether and silicone. The thickener includes, for example, Gua gum, arginic acid, gum arabic, pectin, starch, xanthane gum and gelatin. On the other hand, as the method for formulating an aqueous suspension containing a phospholipid, there may be mentioned, for example, a method wherein a phospholipid such as soybean phospholipid or yolk phospholipid is used instead of the surfactant used in the above method, and an antioxidant such as α-tocopherol is used instead of the thickener.

Further, these formulations may be formed into tablets, capsules, enteric coated tablets, powders, injection solutions or suppositorties by usual methods commonly employed in the field of formulation.

The compounds of the present invention are readily soluble in pharmaceutically acceptable non-aqueous solvents such as medium chain triglyceride, soybean oil, sesami oil, olive oil, tsubaki oil, rapeseed oil, corn oil, peanut oil and cotton seed oil. Accordingly, they can readily be formulated into fatty emulsions for intravenous injection. As a method for formulating such fatty emulsions, there may be mentioned, for example, a method in which a compound of the present invention and a phospholipid are dissolved, if necessary, together with an emulsifying adjuvant and an emulsion stabilizer, in the above-mentioned non-aqueous solvent, and water is added, followed by homogenizing the dispersion by a homogenizer to bring the average particle size to a level of not more than 1.0 μm. As the phospholipid used here, purified yolk phospholipid or soybean phospholipid may be mentioned. As the emulsifying adjuvant, a pharmaceutically acceptable fatty acid having from 6 to 22 carbon atoms, or its alkali metal salt such as a sodium or potassium salt or its alkaline earth metal salt such as a calcium salt, may be employed. As the emulsion stabilizer, cholesterol or phosphatidic acid, may be mentioned. Further, an isotonic agent such as glycerol or glucose may be added to make this fatty emulsion isotonic. The homogenizer used here, may be a pressure spray type homogenizer or an ultrasonic homogenizer.

Now, specific Formulation Examples of the antitumour agent of the present invention will be mentioned.

FORMULATION EXAMPLE 1

70 mg of non-crystalline powder of the aforementioned Compound No. 1 was thoroughly mixed with 30 mg of lactose, and mixture was filled in capsules in an amount of 100 mg per capsule to obtain capsules for oral administration.

FORMULATION EXAMPLE 2

86.5 parts by weight of the non-crystalline powder of the afore-mentioned Compound No. 3 was uniformly mixed with 1 part by weight of glucose, 10 parts by weight of corn starch and 1.5 parts by weight of a 5% corn starch paste solution. The mixture was formed to granules by a wet method. Then, 1 part by weight of magnesium stearate was added thereto, and the mixture was tabletted by compression to obtain tablets for oral administration.

FORMULATION EXAMPLE 3

5 g of the afore-mentioned Compound No. 4 was dissolved in 5 ml of dimethyl acetamide, and 25 ml of coconut oil, 7 g of Pegnol HC-17 (registered trademark, hardened caster oil manufactured by Toho Kagaku) and 6 g of Pegnol HO-10M (registered trademark, sucrose ester manufactured by Toho Kagaku) were added thereto to obtain an emulsion. To this emulsion, the same amount of sterilized distilled water was added, and the mixture was subjected to ultrasonic treatment for 20 to 30 second to obtain an emulsion.

FORMULATION EXAMPLE 4

The afore-mentioned Compound No. 26 was preliminarily pulverized to fine powder by a centrifugal pulverizer. On the other hand, 5 parts by weight of polyoxyethylene (60) hardened castor oil, 0.2 part by weight of silicone and 0.3 part by weight of polyoxyethylenepolyoxypropylene block polymer were added to 79.5 parts by weight of a physiological saline to obtain an aqueous solution. To the aqueous solution, 10 parts by weight of the fine powder of the afore-mentioned Compound No. 3 was added. The mixture was wet pulverized by a sand mill by using glass beads (particles of which 80% had a particle size of at most 2 μm). Then, 5 parts by weight of a 2% xanthane gum solution was added thereto to obtain an aqueous suspension.

FORMULATION EXAMPLE 5

40 parts by weight of the afore-mentioned Compound No. 1 was added to an aqueous solution containing 1.5 parts by weight of oxyethylated polyarylphenol phosphate and 0.2 part by weight of silicone dissolved in 53.3 parts by weight of a physiological saline. The mixture was wet pulverized by a sand mill by using glass beads (particles of which 90% had a particle size of at most 2 μm). Then, 5 parts by weight of a 2% xanthane gum solution was added thereto to obtain an aqueous suspension.

FORMULATION EXAMPLE 6

The afore-mentioned Compound No. 4 was preliminarily pulverized to fine powder by a centrifugal pulverizer. 5 parts by weight of the fine powder of the Compound No. 4 was added to an aqueous solution obtained by dispersing and stirring 2 parts by weight of yolk phospholipid, 0.001 part by weight of u-tocopherol and 92.999 parts by weight of a physiological saline. The mixture was wet pulverized by a sand mill by using glass beads (particles of which 80% had a particle size of at most 2 μm) to obtain an aqueous suspension.

FORMULATION EXAMPLE 7

The afore-mentioned Compound No. 3 was preliminarily pulverized to fine powder by a centrifugal pulverizer. On the other hand, 5 parts by weight of polyoxyethylene (60) hardened castor oil was added to 60 parts by weight of a physiological saline to obtain an aqueous solution. To the aqueous solution, 30 parts by weight of the fine powder of the Compound No. 3 was added. The mixture was wet pulverized by a sand mill by using glass beads (particles of which 80% had a particle size of at most of 2 μm). Then, 5 parts by weight of a 2% xanthane gum solution was added thereto to obtain an aqueous suspension.

FORMULATION EXAMPLE 8

10 parts by weight of the afore-mentioned Compound No. 1 was added to an aqueous solution containing 1.5 parts by weight of oxyethylated polyaryl phosphate, 0.2 part by weight of silicon and 0.3 part by weight of polyoxyethylene-polyoxypropylene block polymer dissolved in 81 parts by weight of a physiological saline. The mixture was wet pulverized by a sand mill by using glass beads (particles of which 90% had a particle size of at most 2 μm). Then, 7 parts by weight of a 2% xanthane gum solution was added thereto to obtain an aqueous suspension.

FORMULATION EXAMPLE 9

To 1 part by weight of the afore-mentioned Compound No. 2, 100 parts by weight of polyethyleneglycol #400 (molecular weight: 380-420, manufactured by Nakarai Kagaku Yakuhin) was added and dissolved to obtain a homogeneous solution.

FORMULATION EXAMPLE 10

2.4 parts by weight of yolk phospholipid and 0.2 part by weight of the afore-mentioned Compound No. 1 were added to 40 parts by weight of medium chain triglyceride (ODO, tradename, manufactured by Nisshin Seiyu K. K.) and dissolved by means of a homomixer. Then, 57.4 parts by weight of distilled water was added thereto. The mixture was roughly emulsified by a homomixer and then emulsified by ultrasonic homogenizer to obtain a fatty emulsion having an average particle size of 1.0 μm.

We claim:

1. A substituted benzoylurea compound of the formula (I):

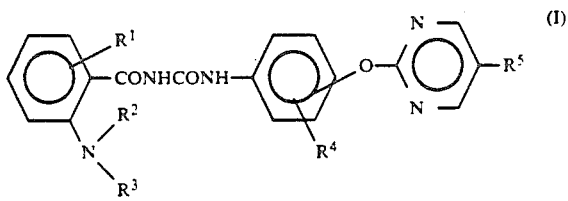

wherein $R^1$ is a hydrogen atom, a halogen atom or a nitro group, each of $R^2$ and $R^3$ is a hydrogen atom, an alkyl group, or $R^2$ and $R^3$ may form together with the adjacent nitrogen atom a heterocyclic ring, $R^4$ is a halogen atom, a alkyl group, a alkoxy group, a alkylthio group or a nitro group, and $R^5$ is a halogen atom, a nitro group or a alkyl group, or its salt.

2. The substituted benzoylurea compound or its salt according to the claim 1, wherein the substituent of the alkyl group, the alkoxy group or the alkylthio group in the definition of $R^4$ is at least one member selected from the group consisting of a halogen atom, an alkoxy group, an alkylthio group, a cyano group, a thiocyanate group, an alkoxycarbonyl group, a carboxyl group and an alkylthiocarbonyl group, the substituent of the alkyl group in the definition of $R^5$ is a halogen atom, and the heterocyclic ring formed by $R^2$ and $R^3$ together with the adjacent nitrogen atom, is a morpholino group, an aziridinyl group, a pyrrolidinyl group, a piperidino group or a pyrrolyl group.

3. The substituted benzoylurea compound or its salt according to claim 1, wherein the benzoylurea compound is of the formula (I'):

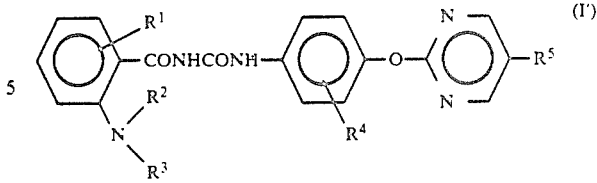

wherein $R^1$, $R^2$, $R^3$, $R^4$ and $R^5$ are as defined above.

4. The substituted benzoylurea compound or its salt according to claim 3, wherein $R^1$ is a hydrogen atom.

5. The substituted benzoylurea compound or its salt according to claim 3, wherein each of $R^2$ and $R^3$ is an alkyl group, or $R^2$ and $R^3$ form together with the adjacent nitrogen atom a heterocyclic ring.

6. The substituted benzoylurea compound or its salt according to claim 3, wherein each of $R^2$ and $R^3$ is an alkyl group.

7. The substituted benzoylufea compound or its salt according to claim 3, wherein $R^4$ is a halogen atom or a alkyl group.

8. The substituted benzoylurea compound or its salt according to claim 3, wherein $R^4$ is a alkyl group.

9. The substituted benzoylurea compound or its salt according to claim 3, wherein $R^5$ is a halogen atom.

10. The substituted benzoylurea compound or its salt according to claim 3, wherein the compound is N-[4-(5-bromo-2-pyrimidinyloxy)-3-methylphenyl]-N'-[2-pyrimidinyloxy)-3-methylphenyl]-N'-[2-urea.hydrochloride, N-[4-(5-bromo-2-pyrimidinyloxy)-3-trifluoromethylphenyl]-N'-[2-(dimethylamino)benzoyl]urea, N-[4-(5-chloro-2-pyrimidinyloxy)-3-trifluoromethylphenyl]-N'-[2(dimethylamino)benzoyl]urea, N-[4-(5-chloro-2-pyrimidinyloxy)-3-methylphenyl]-N'-[2(dimethylamino)benzoyl]urea, N-[4-(5-bromo-2(diethylamino)benzoyl]urea, or N-[4-(5-chloro-2-pyrimidinyloxy)-3-methylphenyl]urea.

11. A composition for treating leukemia, in a mammal, which comprises a compound or its salt as defined in claim 1 in an amount sufficient to exhibit a controlling activity against leukemia and a pharmaceutically acceptable adjuvant.

12. A method for treating leukemia, in a mammal, which comprises administering a compound or its salt as defined in claim 1 in an amount sufficient to exhibit a controlling activity against leukemia.

* * * * *